# (12) United States Patent
Uehara et al.

(10) Patent No.: US 9,248,081 B2
(45) Date of Patent: Feb. 2, 2016

(54) CLEAR LEAVE-ON HAIR CARE COMPOSITION COMPRISING AMINOSILICONE AND ITS SOLVENT

(75) Inventors: Nobuaki Uehara, Kobe (JP); Jun Hasegawa, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/165,070

(22) Filed: Jun. 21, 2011

(65) Prior Publication Data

US 2011/0311471 A1 Dec. 22, 2011

Related U.S. Application Data

(60) Provisional application No. 61/357,185, filed on Jun. 22, 2010, provisional application No. 61/389,297, filed on Oct. 4, 2010.

(51) Int. Cl.
*A61K 8/898* (2006.01)
*A61Q 5/12* (2006.01)
*A61K 8/31* (2006.01)
*A61K 8/891* (2006.01)
*C08L 83/08* (2006.01)
*C08G 77/26* (2006.01)

(52) U.S. Cl.
CPC . *A61K 8/31* (2013.01); *A61K 8/891* (2013.01); *A61K 8/898* (2013.01); *A61Q 5/12* (2013.01); *C08L 83/08* (2013.01); *A61K 2800/30* (2013.01); *A61K 2800/31* (2013.01); *C08G 77/26* (2013.01)

(58) Field of Classification Search
CPC ......... A61K 8/31; A61K 8/891; A61K 8/898; A61K 2800/31; A61K 2800/33
USPC ..................................................... 424/70.122
See application file for complete search history.

(56) References Cited

U.S. PATENT DOCUMENTS

| 5,160,449 A | 11/1992 | Halloran |
| 5,240,689 A | 8/1993 | Jones |
| 5,679,331 A * | 10/1997 | Hague et al. ............... 424/70.19 |
| 2005/0063934 A1 * | 3/2005 | Baker et al. .............. 424/70.122 |

FOREIGN PATENT DOCUMENTS

| EP | 0479000 | 4/1992 |
| JP | 2005002037 | 1/2005 |
| JP | 2006249002 | 9/2006 |
| JP | 2009-203212 | 9/2009 |
| WO | WO 01/91706 A1 * | 12/2001 |
| WO | WO2004010967 | 2/2004 |
| WO | WO2005030153 | 7/2005 |
| WO | WO2008142658 A2 | 11/2008 |

OTHER PUBLICATIONS

Material Safety Data Sheet for Isopar C Solvent (Esso Imperial Oil, accessed on Dec. 29, 2013, http://doc.ccc-group.com/msds/english/507110.pdf).*
International Search Report; PCT/US2011/041210; 9 pages.

* cited by examiner

*Primary Examiner* — Richard Schnizer
*Assistant Examiner* — Alma Pipic
(74) *Attorney, Agent, or Firm* — Linda M. Sivik

(57) ABSTRACT

Disclosed is a hair care composition comprising: a specific aminosilicone; a solvent for the aminosilicone; wherein the composition is for leave-on use; and wherein the composition has a turbidity of 2.0 NTU or less. The compositions of the present invention provide improved dry conditioning benefits such as reduced friction.

4 Claims, No Drawings"

CLEAR LEAVE-ON HAIR CARE COMPOSITION COMPRISING AMINOSILICONE AND ITS SOLVENT

CROSS REFERENCE TO RELATED APPLICATIONS

This application claims the benefit of U.S. Provisional Application No. 61/357,185 filed on Jun. 22, 2010 and U.S. Provisional Application No. 61/389,297 dated Oct. 4, 2010.

FIELD OF THE INVENTION

The present invention relates to a hair care composition comprising: a specific aminosilicone; a solvent for the aminosilicone; wherein the composition is for leave-on use; and wherein the composition has a turbidity of 2.0 NTU or less. The compositions of the present invention provide improved dry conditioning benefits such as reduced friction.

BACKGROUND OF THE INVENTION

Human hair becomes soiled due to its contact with the surrounding environment and from the sebum secreted by the scalp. The soiling of hair causes it to have a dirty feel and an unattractive appearance. The soiling of the hair necessitates shampooing with frequent regularity.

Shampooing cleans the hair by removing excess soil and sebum. However, shampooing can leave the hair in a wet, tangled, and generally unmanageable state. Once the hair dries, it is often left in a dry, rough, lusterless, or frizzy condition due to removal of the hair's natural oils and other natural conditioning and moisturizing components. The hair can further be left with increased levels of static upon drying, which can interfere with combing and result in a condition commonly referred to as "fly-away hair," or contribute to an undesirable phenomenon of "split ends." Further, chemical treatments, such as perming, bleaching, or coloring hair, can also damage hair and leave it dry, rough, lusterless, and damaged.

A variety of approaches have been developed to condition the hair. A common method of providing conditioning benefits to the hair is through the use of application of hair conditioning composition. Conditioning formulations can be in the form of rinse-off products or leave-on products, and can be in the form of an emulsion, cream, gel, spray, mousse, oil, liquid and serum.

For leave-on products especially those in a liquid form (such as oil, liquid and serum), silicone oils such as dimethylpolysiloxane and/or aminosilicones are often used. However, there remains a need for such products to provide improved dry conditioning benefits such as reduced friction.

Additionally, there may be a need for leave-on products to provide reduced sticky/greasy feeling, while providing such conditioning benefits like reduced friction.

Furthermore, there may be a need for leave-on products especially those in a liquid form, to have a homogeneous clear product appearance as such appearance may be perceived as a signal of reduced sticky/greasy feeling.

None of the existing art provides all of the advantages and benefits of the present invention.

SUMMARY OF THE INVENTION

The present invention is directed to a hair care composition comprising: an aminosilicone having a formula:

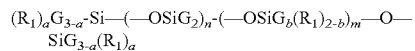

$(R_1)_a G_{3-a}\text{-Si}-(-OSiG_2)_n\text{-}(-OSiG_b(R_1)_{2-b})_m-O-SiG_{3-a}(R_1)_a$ wherein G is hydrogen, phenyl, hydroxy, or $C_1$-$C_8$ alkyl; a is an integer having a value from 1 to 3; b is 0, 1 or 2; n is a number from 1 to 2,000; m is 0; $R_1$ is a monovalent radical conforming to the general formula $CqH_{2q}L$, wherein q is an integer having a value from 2 to 8 and L is selected from the following groups: $-N(R_2)CH_2-CH_2-N(R_2)_2$; $-N(R_2)_2$; $-N(R_2)_3 A^-$; $-N(R_2)CH_2-CH_2-NR_2H_2A^-$; wherein $R_2$ is hydrogen, phenyl, benzyl, or a saturated hydrocarbon radical; $A^-$ is a halide ion;

a solvent for the aminosilicone;

wherein the composition is for leave-on use; and wherein the composition has a turbidity of 2.0 NTU or less.

The hair care compositions of the present invention provide improved dry conditioning benefits such as reduced friction, and also provide clear product appearance.

These and other features, aspects, and advantages of the present invention will become better understood from a reading of the following description, and appended claims.

DETAILED DESCRIPTION OF THE INVENTION

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "mixtures" is meant to include a simple combination of materials and any compounds that may result from their combination.

Composition

It is believed that the use of the specific aminosilicone of the present invention provides improved dry conditioning benefit such as reduced friction. It is also believed that, such specific aminosilicone may provide product clarity in a larger amount and/or in a wider combination with volatile solvent, compared to other silicones. It is further believed that, such specific aminosilicone may provide reduced stickiness/greasiness while providing sufficient dry conditioning benefit, compared to other silicones.

Turbidity

The composition of the present invention has a homogeneous clear product appearance, i.e., homogeneous transparent product appearance.

Preferably, the composition of the present invention has a turbidity of 2.0 NTU or less, 1.5 NTU or less, more preferably 1.0 NTU or less, still more preferably 0.7 NTU or less at 25° C. Further preferably, the composition of the present invention has such above turbidity at 25° C., even after its storage at 5° C. for at least 1 hour. The turbidity is measured by using HACH 2100N Turbidimeter.

In view of homogeneous clear product appearance, it is preferred to control the level of components which are substantially insoluble to the composition of the present invention. By "substantially insoluble" compound, what is meant is that:

the compound is substantially insoluble in the compositions at the level used; and, when containing the compounds at the level used, the compositions are either: (i) non-homogeneous by, for example, phase separation; or (ii) homogeneous but with a higher turbidity, i.e., turbidity of above 2.0 NTU (excluding 2.0 NTU), preferably above 1.5 NTU (excluding 1.5 NTU), more preferably above 1.0 NTU (excluding 1.0 NTU), still more preferably above 0.7 NTU (excluding 0.7 NTU) at 25° C.

Such substantially insoluble compounds include fatty compounds including, for example: fatty alcohols having a melting point of 25° C. or more, such as cetyl alcohol and stearyl alcohol; fatty acids having a melting point of 25° C. or more, such as stearic acid; fatty alcohol derivatives and fatty acid derivatives such as esters and ethers thereof, which derivatives have a melting point of 25° C. or more; and mixtures thereof.

More preferably, the compositions of the present invention are substantially free of such substantially insoluble compounds. In the present invention, the compositions being "substantially free" of substantially insoluble compounds means that: the composition is free of substantially insoluble compounds; or, if the composition contains substantially insoluble compounds, the level of such substantially insoluble compounds is very low. In the present invention, the level of such substantially insoluble compounds is, if included, 1.0% or less, preferably 0.5% or less, more preferably 0.3% or less, still more preferably 0.1% or less, even more preferably 0%.

Preferably, the composition of the present invention is substantially free of anionic surfactants, in view of skin irritation and/or product clarity. In the present invention, "the composition being substantially free of anionic surfactants" means that: the composition is free of anionic surfactants; or, if the composition contains anionic surfactants, the level of such anionic surfactants is very low. In the present invention, the total level of such anionic surfactants is, if included, 1% or less, preferably 0.5% or less, more preferably 0.1% or less by weight of the composition.

Aminosilicone

The composition of the present invention comprises an aminosilicone which is explained below in detail. The aminosilicone is used at levels by weight of the composition of, preferably from about 0.1%, more preferably from about 0.2%, in view of providing dry conditioning benefit such as reduced friction, and preferably to about 15%, more preferably to about 10%, still more preferably to about 8%, in view of reduced stickiness/greasiness and/or product clarity.

Preferably, aminosilicones useful herein have an amine content of less than about 0.12 m mol/g, more preferably less than about 0.1 m mol/g, still more preferably less than about 0.08 m mol/g, even more preferably less than about 0.06 m mol/g, in view of friction reduction benefit. It has been surprisingly found that higher levels of nitrogen (amine functional groups) in the amino silicone tend to result in less friction reduction, and consequently less conditioning benefit from the aminosilicone.

Aminosilicone useful herein are those which conform to the general formula (I):

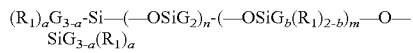

wherein G is hydrogen, phenyl, hydroxy, or $C_1$-$C_8$ alkyl, preferably methyl; a is an integer having a value from 1 to 3, preferably 1; b is 0, 1 or 2, preferably 1; n is a number from 1 to 2,000, preferably from 100 to 1,800, more preferably from 300 to 800, still more preferably 500-600; m is 0; $R_1$ is a monovalent radical conforming to the general formula $CqH_{2q}L$, wherein q is an integer having a value from 2 to 8 and L is selected from the following groups: —$N(R_2)CH_2$—$CH_2$—$N(R_2)_2$; —$N(R_2)_2$; —$N(R_2)_3A^-$; —$N(R_2)CH_2$—$CH_2$—$NR_2H_2A^-$; wherein $R_2$ is hydrogen, phenyl, benzyl, or a saturated hydrocarbon radical, preferably an alkyl radical from about $C_1$ to about $C_{20}$; $A^-$ is a halide ion. L is preferably —$N(CH_3)_2$ or —$NH_2$, more preferably —$NH_2$.

One highly preferred amino silicones are those corresponding to formula (I) wherein m=0, a=1, q=3, G=methyl, n is preferably from about 1400 to about 1700, more preferably around 1600; and L is —$N(CH_3)_2$ or —$NH_2$, more preferably —$NH_2$. Another further highly preferred amino silicones are those corresponding to formula (I) wherein m=0, a=1, q=3, G=methyl, n is preferably from about 400 to about 800, more preferably about 500 to around 600; and L is —$N(CH_3)_2$ or —$NH_2$, more preferably —$NH_2$.

Such preferred aminosilicones can be called as terminal aminosilicones, as one or both ends of the silicone chain are terminated by nitrogen containing group. It is also surprisingly found that, such terminal aminosilicones provide improved friction reduction compared to graft aminosilicones.

Solvent

The compositions of the present invention comprise a solvent for the above aminosilicone. Such solvent is used at levels by weight of the composition of from about 30% to about 99.9%, more preferably from about 40% to about 99.8%.

The solvent can be selected according to the compatibility with the above aminosilicone for solving it, and for providing product clarity and, if any, other desired characteristic of the composition of the present invention. The solvent useful herein are, for example, those selected from the group consisting of an isoparaffin hydrocarbon having a viscosity of from about 0.5 $mm^2 \cdot s^{-1}$ to about 50 $mm^2 \cdot s^{-1}$, a volatile silicone compound having from 2 to 7 silicon atoms, and mixtures thereof. The solvent useful herein is believed to reduce sticky and greasy feeling, and leave the hair and hands with a clean feeling.

Isoparaffin Hydrocarbons

The isoparaffin hydrocarbons useful herein have a viscosity of, preferably from about 0.5 $mm^2 \cdot s^{-1}$ to about 50 $mm^2 \cdot s^{-1}$, more preferably from about 0.8 $mm^2 \cdot s^{-1}$ to about 40 $mm^2 \cdot s^{-1}$, still more preferably from about 1 $mm^2 \cdot s^{-1}$ to about 30 $mm^2 \cdot s^{-1}$, even more preferably from about 1.5 $mm^2 \cdot s^{-1}$ to about 20 $mm^2 \cdot s^{-1}$, at 37.8° C., in view of balance between reduced sticky/greasy feel and conditioned feel which could be delivered by a higher viscosity. When using two or more isoparaffin hydrocarbon solvents, it is preferred that the mixture of isoparaffin hydrocarbon solvents have the above viscosity. In the present invention, preferred isoparaffin hydrocarbons include, for example, trimer, tetramer, pentamer, and hexamer of isobutene, and mixtures thereof. Commercially available isoparaffin hydrocarbons may have distributions of its polymerization degree, and may be mixtures of, for example, trimer, tetramer, pentamer, and hexamer. What is meant by tetramer herein is that a commercially available isoparaffin hydrocarbons in which tetramer has the highest content, i.e., tetramer is included at a level of preferably 70% or more, more preferably 80% or more, still more preferably 85% or more.

As for such isoparaffin hydrocarbons, especially when pentamer, hexamer, and further larger polymer of isobutene are used, they can be used in combination with ethanol in view of providing reduced stickiness/greasiness. In one embodiment of the present invention, for example, a mixture of tetramer and hexamer of isobutenes are used in the presence of ethanol. In such mixture of tetramer and hexamer of isobutenes, tetramer and hexamer can be present at a ratio of, preferably from about 10:90 to about 60:40, more preferably from about 15:85 to about 55:45, still more preferably from about 25:75 to about 45:55. Ethanol can be present in the composition at a level by weight of the composition of, preferably from about 0.1% to about 15%, more preferably from about 0.3% to about 10%, still more preferably from about 0.5% to about 8%, even more preferably from about 1% to about 7%.

Alternatively, in view of providing reduced stickiness/greasiness while providing a certain viscosity, a mixture of larger polymer of isobutenes and smaller polymer of isobutenes can be used, with or without the presence of ethanol, preferably without the presence of ethanol. Such larger polymers of isobutenes include, for example, pentamer, hexamer or larger polymer of isobutenes. Such smaller polymers of isobutenes include, for example, trimer and tetramer of isobutenes. In one embodiment of the present invention, for example, a mixture of trimer, tetramer and hexamer of isobutenes are used without the presence of ethanol. In such mixture, ratio of the smaller polymers of isobutenes to the larger polymer of isobutenes can be, for example, from about 10:90 to about 60:40, preferably from about 15:85 to about 55:45, more preferably from about 25:75 to about 45:55.

Volatile Silicone Compounds

The volatile silicone compounds useful herein include polyalkyl or polyaryl siloxanes with the following structure (I):

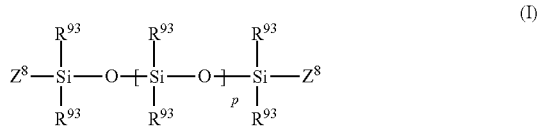

wherein $R^{93}$ is independently alkyl or aryl, and x is an integer from about 0 to about 5. $Z^8$ represents groups which block the ends of the silicone chains. Preferably, $R^{93}$ groups include methyl, ethyl, propyl, phenyl, methylphenyl and phenylmethyl, $Z^8$ groups include hydroxy, methyl, methoxy, ethoxy, propoxy, and aryloxy. More preferably, $R^{93}$ groups and $Z^8$ groups are methyl groups. The preferred volatile silicone compounds are hexamethyldisiloxane, octamethyltrisiloxane, decamethyltetrasiloxane, hexadecamethylheptasiloxane. Commercially available volatile silicone compounds useful herein include octamethyltrisiloxane with tradename SH200C-1cs, decamethyltetrasiloxane with tradename SH200C-1.5cs, hexadecamethylheptasiloxane with tradename SH200C-2cs, all available from Dow Corning.

The volatile silicone compounds useful herein also include a cyclic silicone compound having the formula:

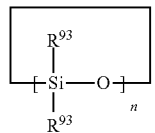

wherein $R^{93}$ is independently alkyl or aryl, and n is an integer of from 3 to 7. Preferably, $R^{93}$ groups include methyl, ethyl, propyl, phenyl, methylphenyl and phenylmethyl. More preferably, $R^{93}$ groups are methyl groups. The preferred volatile silicone compounds are octamethylcyclotetrasiloxane, decamethylcyclopentasiloxane, tetradecamethylcyclohexasiloxane. Commercially available volatile silicone compounds useful herein include octamethylcyclotetrasiloxane with tradename SH244, decamethylcyclopentasiloxane with tradename DC 345 all available from Dow Corning.

Mineral Oil

The composition of the present invention may further contain a mineral oil. Mineral oils useful herein are those having a viscosity of, preferably from about 0.5 mm²·s⁻¹ to about 50 mm²·s⁻¹, more preferably from about 0.8 mm²·s⁻¹ to about 40 mm²·s⁻¹, still more preferably from about 1 mm²·s⁻¹ to about 30 mm²·s⁻¹, even more preferably from about 1.5 mm²·s⁻¹ to about 20 mm²·s⁻¹, at 37.8° C., in view of balance between reduced sticky/greasy feel and conditioned feel which could be delivered by a higher viscosity.

Mineral oils can be included at a level by weight of the composition of, preferably from about 1% to about 70%, more preferably from about 3% to about 65%, still more preferably from about 5% to about 60%.

Non-Aqueous Composition

The composition of the present invention is a non-aqueous composition. Non-aqueous composition herein means that the composition is substantially free of water. In the present invention, "the composition being substantially free of water" means that: the composition is free of water; or, if the composition contains water, the level of water is very low. In the present invention, the level of water, if included, 1% or less, preferably 0.5% or less, more preferably 0.3% or less, still more preferably 0.1% or less, even more preferably 0% by weight of the composition.

Additional Components

The composition of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

A wide variety of other additional components can be formulated into the present compositions. These include: other conditioning agents such as hydrolysed collagen with tradename Peptein 2000 available from Hormel, vitamin E with tradename Emix-d available from Eisai, panthenol available from Roche, panthenyl ethyl ether available from Roche, hydrolysed keratin, proteins, plant extracts, and nutrients; preservatives such as benzyl alcohol, methyl paraben, propyl paraben and imidazolidinyl urea; coloring agents, such as any of the FD&C or D&C dyes; perfumes; and antidandruff agents such as zinc pyrithione and salicylic acid.

Product Forms

The hair care compositions of the present invention can be hair conditioning and/or hair styling products, and the like.

The hair care compositions of the present invention are in the form of leave-on products, and can be formulated in a wide variety of product forms, including but not limited to gels, sprays, oils, liquid and serum. Preferably, the compositions of the present invention are in a liquid form such as oil, liquid and serum.

Method of Use

For a leave-on form, the hair care composition is preferably applied to wet or damp hair prior to drying of the hair. After such hair care compositions are applied to the hair, the hair is dried and styled in accordance with the preference of the user. In the alternative, it may be applied to already dry hair, and the hair is then combed or styled, and dried in accordance with the preference of the user.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

Properties and Conditioning Benefits

Turbidity is measured by the method described above. For some of the compositions, conditioning benefits are evaluated by the following methods. The results of the evaluation are shown above.

Dry Conditioning

Dry conditioning performance is evaluated by hair friction force measured by an instrument named Instron Tester (Instron 5542, Instron, Inc.: Canton, Mass., USA). 1 g of the composition is applied to 20 g of hair sample. After spreading the composition on the wet hair sample, the hair sample is left to dry over night at 45% room humidity at 23° C. The friction force (g) between the hair surface and a natural rubber pad along the hair is measured.

[Compositions]

| Components | Ex. 1 | Ex. 2 | Ex. 3 | Ex. 4 | Ex. 5 | Ex. i | Ex. ii | Ex. iii | Ex. iv |
|---|---|---|---|---|---|---|---|---|---|
| Aminosilicone-1 *1 | 5.0 | 0.5 | 2.0 | 2.0 | — | — | — | — | — |
| Aminosilicone-2 *2 | — | — | — | — | 1.0 | — | — | — | — |
| Graft aminosilicone *3 | — | — | — | — | — | 2.0 | 2.0 | — | — |
| Dimethicone fluid *4 | — | — | — | — | — | — | — | 2.0 | 2.0 |
| Volatile silicone *5 | — | — | q.s. to 100% | — | — | q.s. to 100% | — | q.s. to 100% | — |
| Volatile isoparaffin-1 *6 | 30 | q.s. to 100% | — | q.s. to 100% | q.s. to 100% | — | q.s. to 100% | — | q.s. to 100% |
| Volatile isoparaffin-2 *7 | — | 10 | — | — | — | — | — | — | — |
| Volatile isoparaffin-3 *8 | q.s. to 100% | — | — | — | — | — | — | — | — |
| Ethanol | 3.0 | — | — | — | 1.0 | — | — | — | — |
| Perfume | 0.4 | 0.4 | 0.4 | 0.4 | 0.35 | 0.25 | 0.25 | 0.25 | 0.4 |
| Turbidity (NTU) at 25° C. | <0.7 | <0.7 | <0.7 | <0.7 | <0.7 | <0.7 | <0.7 | <0.7 | <0.7 |
| Dry conditioning | — | — | A | A | — | D | D | C | F |

[Compositions]

| Components | Ex.6 | Ex.7 |
|---|---|---|
| Aminosilicone-1 *1 | 2.0 | 2.0 |
| Volatile isoparaffin-1 *6 | 25 | — |
| Volatile isoparaffin-2 *7 | — | q.s. to 100% |
| Volatile isoparaffin-3 *8 | q.s. to 100% | — |
| Volatile isoparaffin-4 *9 | 30 | — |
| Perfume | 0.4 | 0.4 |
| Turbidity (NTU) at 25° C. | <0.7 | <0.7 |
| Dry conditioning | — | — |

Definitions of Components

*1 Aminosilicone-1: Terminal aminosilicone which is available from GE having a viscosity of about 10,000 mPa · s, and having following formula: $(R_1)_aG_{3-a}$—Si$(-OSiG_2)_n(-OSiG_b(R_1)_{2-b})_m$—O—$SiG_{3-a}(R_1)_a$ wherein G is methyl; a is an integer of 1; n is a number from 400 to about 600; m is an integer of 0; $R_1$ is a monovalent radical conforming to the general formula $C_qH_{2q}L$, wherein q is an integer of 3 and L is —$NH_2$

*2 Aminosilicone-2: Terminal aminosilicone which is available from GE having a viscosity of about 230,000 mPa · s, and having following formula: $(R_1)_aG_{3-a}$—Si$(-OSiG_2)_n(-OSiG_b(R_1)_{2-b})_m$—O—$SiG_{3-a}(R_1)_a$ wherein G is methyl; a is an integer of 1; n is a number from 1,500 to about 1,700; m is an integer of 0; $R_1$ is a monovalent radical conforming to the general formula $C_qH_{2q}L$, wherein q is an integer of 3 and L is —$N_2$

*3 Graft Aminosilicone: AP 6087 fluid available from Dow Corning

*4 Dimethicone Fluid: 15%/85% mixture of dimethicone having a viscosity of 18,000,000 mPa · s and dimethicone having a viscosity of 200 mPa · s

*5 Volatile Silicone: Decamethylcyclopentasiloxane

*6 Volatile Isoparaffin-1: Tetramer of isobutene, available from Idemitsu as IP Solvent 2028MU

*7 Volatile Isoparaffin-2: Pentamer of isobutene, available from NOF as Parleam EX

*8 Volatile Isoparaffin-3: Hexamer of isobutene, available from NOF as Parleam 6

*9 Volatile Isoparaffin-4: Trimer of isobutene, available from Idemitsu as IP Solvent 1620MU Method of Preparation The hair conditioning compositions of "Ex. 1" through "Ex. 7" and "Ex. i" through "Ex. iv" as shown above can be prepared by any conventional method well known in the art. They are suitably made as follows:

Silicones are added to solvents with agitation at room temperature until homogenized. If included, other components such as perfumes are added to the mixture with agitation.

A: Above 35% (excluding 35%) to 45% reduction of Friction force, compared to Control B: Above 25% (excluding 25%) to 35% reduction of Friction force, compared to Control C: Above 15% (excluding 15%) to 25% reduction of Friction force, compared to Control D: Above 5% (excluding 5%) to 15% reduction of Friction force, compared to Control E: Up to 5% (including 5%) reduction of Friction force, compared to Control F: Control Examples 1 through 7 are hair conditioning compositions of the present invention which are particularly useful for leave-on use. The embodiments disclosed and represented by the previous "Ex. 1" through "Ex. 7" have many advantages. For example, they improved dry conditioning benefits such as reduced friction, while providing clear product appearance.

Such advantages can be understood by the comparison between the examples of the present invention and comparative examples "Ex. i" through "Ex. iv". For example, the compositions of the present invention "Ex. 3" and "Ex.4" shows improved dry conditioning, compared to the compositions of comparative examples "Ex.i" through "Ex. iv".

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair care composition comprising by weight:
   from about 0.2% to about 8% of an aminosilicone having a formula:

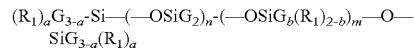

wherein G is hydrogen, phenyl, hydroxy, or $C_1$-$C_8$ alkyl; a is an integer having a value from 1 to 3; b is 0, 1 or 2; n is a number from 1 to 2,000; m is 0; $R_1$ is a monovalent radical having the general formula $C_qH_{2q}L$, wherein q is an integer having a value from 2 to 8 and L is selected from the group consisting of —$N(R_2)CH_2$—$CH_2$—$N(R_2)_2$, —$N(R_2)_2$, —$N(R_2)_3A^-$, and —$N(R_2)CH_2$—$CH_2$—$NR_2H_2A^-$, wherein $R_2$ is hydrogen, phenyl, benzyl, or a saturated hydrocarbon radical, and $A^-$ is a halide ion; and from about 40% to about 99.8% of a solvent for the aminosilicone;

wherein the solvent is an isoparaffin hydrocarbon having a viscosity of from about 0.5 $mm^2 \cdot s^{-1}$ to about 50 $mm^2 \cdot s^{-1}$ wherein the isoparaffin hydrocarbon is a mixture of larger polymers of isobutene and smaller polymers of isobutene, such larger polymers of isobutene being selected from the group consisting of pentamer, hexamer, and larger polymer of isobutenes, and such smaller polymers of isobutene being selected from the group consisting of trimer and tetramer of isobutene, and wherein a ratio of the smaller polymers of isobutene to the larger polymers of isobutene is from 25:75 to 45:55 by weight; wherein the composition is a non-aqueous composition for leave-on use; and wherein the composition has a turbidity of 2.0 NTU or less.

2. The hair care composition of claim 1 wherein the aminosilicone has the formula:

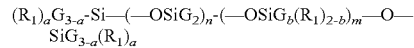

wherein G is hydrogen, phenyl, hydroxy, or $C_1$-$C_8$ alkyl; a is 1; n is a number from 100 to 1,800; m is 0; $R_1$ is a monovalent radical having the general formula $C_qH_{2q}L$, wherein q is an integer having a value from 2 to 8 and L is —$N(R_2)_2$; wherein $R_2$ is hydrogen, phenyl, benzyl, or a saturated hydrocarbon radical; and A is a halide ion.

3. The hair care composition of claim 1 wherein L is —$N(CH_3)_2$ or —$NH_2$.

4. The hair care composition of claim 1 wherein the composition is free of anionic surfactants.

* * * * *